United States Patent [19]

Levine et al.

[11] Patent Number: 5,868,754
[45] Date of Patent: Feb. 9, 1999

[54] MEDICAL RETRIEVAL DEVICE

[75] Inventors: Marc-Alan Levine, Fremont; Son M. Gia, San Jose; Mehran Bashiri, Fremont; David Kupiecki, Cupertino, all of Calif.

[73] Assignee: Target Therapeutics, Inc., Fremont, Calif.

[21] Appl. No.: 662,322

[22] Filed: Jun. 12, 1996

[51] Int. Cl.$^6$ .............................. A61F 11/00; A61B 17/00; A61B 17/08
[52] U.S. Cl. ................................. 606/108; 606/1; 606/151
[58] Field of Search ................................ 606/151, 1, 106, 606/108, 113, 127, 198, 213, 159

[56] References Cited

U.S. PATENT DOCUMENTS

| | | |
|---|---|---|
| 892,472 | 7/1908 | Walker . |
| 894,198 | 7/1908 | Funk . |
| 2,767,703 | 10/1956 | Nieburgs . |
| 3,174,851 | 3/1965 | Buehler et al. . |
| 3,351,463 | 11/1967 | Rozner et al. . |
| 3,753,700 | 8/1973 | Harrison et al. . |
| 3,868,956 | 3/1975 | Alfidi et al. . |
| 4,030,503 | 6/1977 | Clark, III . |
| 4,174,715 | 11/1979 | Hasson . |
| 4,494,531 | 1/1985 | Gianturco . |
| 4,612,931 | 9/1986 | Dormia . |
| 4,654,028 | 3/1987 | Suma . |
| 4,655,219 | 4/1987 | Petruzzi . |
| 4,807,626 | 2/1989 | McGirr . |
| 4,873,978 | 10/1989 | Ginsburg . |
| 4,909,789 | 3/1990 | Tagachi et al. . |
| 4,990,151 | 2/1991 | Wallstén . |
| 4,994,069 | 2/1991 | Ritchart et al. . |
| 5,057,114 | 10/1991 | Wittich et al. . |
| 5,098,440 | 3/1992 | Hillstead . |
| 5,122,136 | 6/1992 | Guglielmi et al. . |
| 5,143,085 | 9/1992 | Wilson . |
| 5,152,777 | 10/1992 | Goldberg et al. . |
| 5,195,954 | 3/1993 | Schnepp-Pesch et al. . |
| 5,226,911 | 7/1993 | Chee et al. . |
| 5,330,482 | 7/1994 | Gibbs et al. . |
| 5,354,295 | 10/1994 | Guglielmi et al. . |
| 5,376,094 | 12/1994 | Kline . |
| 5,387,219 | 2/1995 | Rappe . |
| 5,405,360 | 4/1995 | Tovey ...................................... 606/151 |
| 5,498,249 | 3/1996 | Quinn . |
| 5,522,819 | 6/1996 | Graves et al. ........................... 606/110 |

*Primary Examiner*—Glenn K. Dawson
*Attorney, Agent, or Firm*—Morrison & Foerster

[57] ABSTRACT

This is a device for capturing and removing bodies or articles from within a vessel, such vessels as may be found in the vascular system or the genital urinary tract. It includes a core wire which has attached at its distal end a plurality of fibers. The core wire may be introduced through a catheter to a selected site and further advanced and "twirled" to engage the offending foreign body. The retriever and its targeted foreign body are then withdrawn using the catheter.

35 Claims, 3 Drawing Sheets

MEDICAL RETRIEVAL DEVICE

FIELD OF THE INVENTION

This invention is a medical device for capturing and removing bodies or articles from within a vessel, such vessels as may be found in the vascular system or the genito-urinary tract.

BACKGROUND OF THE INVENTION

Vaso-occlusive devices, particularly helically wound coils, are surgical implements that may be placed within vessels or other openings in the human body. Although more widely used as devices to block the flow of blood through a vascular lumen, such devices may also be used to block other body lumen such as fallopian tubes or bile ducts or the like. Widely known and used a variant of the vaso-occlusive device class is a helically wound coil which, after having been given a primary form, is wound into a second form. The vaso-occlusive device is typically delivered through a catheter having a small interior lumen. The devices having secondary forms are constructed to such a way that they conform to the shape of the interior of the catheter during the period they are being deployed. After exiting the distal tip of the catheter, the device will then often attain the secondary shape discussed just above.

U.S. Pat. No. 4,994,069 describes a vaso-occlusive coil having a linear helical configuration when stretched and having a folded, convoluted configuration when relaxed. The stretched or primary condition is used when placing the coil at a desired site within the body. The coil assumes its relaxed configuration once the device is properly placed within the body. The secondary shape is one which is better suited to occlude the vessel or opening in the body.

U.S. Pat. No. 5,226,911, to Chee et al, shows a variation of the vaso-occlusive coil in which a number of fibrous elements are attached to the coil so to enhance the thrombogenicity of the coil assembly.

Still another variation of the vaso-occlusive coil is described in U.S. Pat. Nos. 5,122,136 and 5,354,295, both to Guglielmi et al. In these variations of the generic vaso-occlusive device, the helically wound coils or wires are maintained in mechanical connection with the pusher wire which propels the coils through the delivery catheter. The connection between vaso-occlusive coil and delivery or core wire is through the use of electrolysis in the joint between the two sections. The Guglielmi et al. devices have the significant benefit in that as the physician places the coil in the human body, the placement is precise prior to the step of severing the mechanical connection.

It may be desirable in some instances to either remove a vaso-occlusive device which has been mal-placed within the human body or to retrieve a section of surgical implement which has been allowed loose within the body. A variety of retrievers are available for such service.

U.S. Pat. No. 5,387,219, to Rappe, shows a medical retrieval snare suitable for retrieving foreign bodies from inside the vasculature. The Rappe device uses a core wire which passes through a tubular body, out the distal end, and is attached at the distal end so to form a single loop. This loop is used to snare, e.g. a vaso-occlusive coil and withdraw it through the guide catheter. Its use relies upon the skill of the attending physician in manipulating the snare so that it "lassoes" the offending device.

Other devices are recognized for the purpose of removing objectionable materials from within the human body. One such device is an embolectomy catheter described in U.S. Pat. No. 4,030,503, to Clark, III. In this device, a spiral coil or auger is placed at the tip of a catheter so that it may be turned and screwed into the thrombus and then pulled out of the vessel. The clot is said to become dislodged from the vessel and generally comes out with the catheter. U.S. Pat. No. 4,174,715 shows a device characterized as a multi-pronged laparoscopy forceps. The forceps found at the end of the catheter assembly are of a somewhat typical design in that they have pinchers which are aligned in such a way as the forceps assembly is retracted into the catheter, the forceps' fingers pinch together for grasping an object.

U.S. Pat. No. 4,654,028, to Suma, describes a device having a number of prongs located on the end of a long wire placed within a tubing assembly. These prongs are positioned so that they are able to inosculate a blood vessel—that is hold an incision open— during the period that a graft is being installed. A similar appearing device is found in U.S. Pat. No. 4,655,219 to Petruzzi. This patent describes a manipulative or grasping assembly adapted for use in conjunction with various endoscopic instruments. The tool is one having an elongated shaft with resilient, flexible fingers at the distal end. The tubular sheath is attached in such a way that it forms a sliding platform and operates as a control mechanism to engage an object using the flexible fingers of the shaft.

Another design for extracting foreign objects from the body is shown in U.S. Pat. No. 4,807,626, to McGirr. This extractor device includes a self closing basket at the distal end of a catheter. The basket closes automatically about a captured object when the control line is released.

U.S. Pat. No. 4,873,978 to Ginsburg, shows a device for catching emboli from the bloodstream. It is a strainer which is collapsible within a catheter. The strainer may be placed within a vessel and is of such a configuration that blood flows through the strainer. When an embolus passes to its vicinity it is caught in the netted strainer device. The strainer may then be collapsed, enclosing the embolus, and withdrawn through the allied catheter.

U.S. Pat. No. 4,909,789, to Tagachi et al, shows a device characterized as "observation assisting forceps." An inner shaft member is placed within a tubular hollow sheath. The distal end of the shaft member has a number of tipped fingers which are biased to expand radially when the interior shaft member is pushed distally out of the hollow sheath. The primary use of the device is to move aside organs and the like when making an observation with an endoscope.

U.S. Pat. No. 4,990,151, to Wallstein, shows a device for implantation or extraction of stents using a multi-fingered device and a catheter with an interior actuating rod.

U.S. Pat. No. 5,098,440, to Hillstead shows a tubular catheter having a pair of opposing wire loops which may be manipulated from outside the body. In general the device is used to remove previously employed stent from the body.

U.S. Pat. No. 5,376,094, to Kline, shows a medical device which may be used as a medical snare to remove articles from the body. Among the structures disclosed as various types of snares are the cages, loops, and forceps shown in, e.g., FIGS. 8 through 17.

None of these devices which may be inserted into the body through various tubular access devices uses the concept found in the inventive retriever structure described below.

SUMMARY OF THE INVENTION

This invention is a medical retrieval device for capturing and removing bodies from within an opening within the human body. The opening may be variously a vessel, open region such an aneurysm, or a duct. In general, the device includes a core wire which is produced in a manner similar to guide wires used in endovascular catheterization procedures. The core wire preferably has a small loop attached at its distal tip. Passing through the loop and perhaps tied or otherwise attached to the shaft of the core wire just distal of the tip are at least one fiber which extends radially from the guide wire for a significant distance, e.g., an inch or more, from the axis of the core wire. The ends of the fibers may have fiber terminators such as balls or small coils which are secured to those fibers. The fibers may be simply heated to form a polymeric terminator or "lump" at the fiber ends.

Distal of the loop in the core wire may be found a shielded hook so to help in retrieval of a vaso-occlusive devices.

The device is used in conjunction with a tubular catheter. The core wire having the fibrous distal appendage is inserted through the lumen of a catheter to a site near the object to be removed from the body. The retriever is both twisted and advanced to the object to be removed and is allowed to become entangled with that undesired object. The object may either be retracted to within the endovascular catheter or perhaps through the larger surrounding guide catheter.

DESCRIPTION OF THE INVENTION

Figure 1:
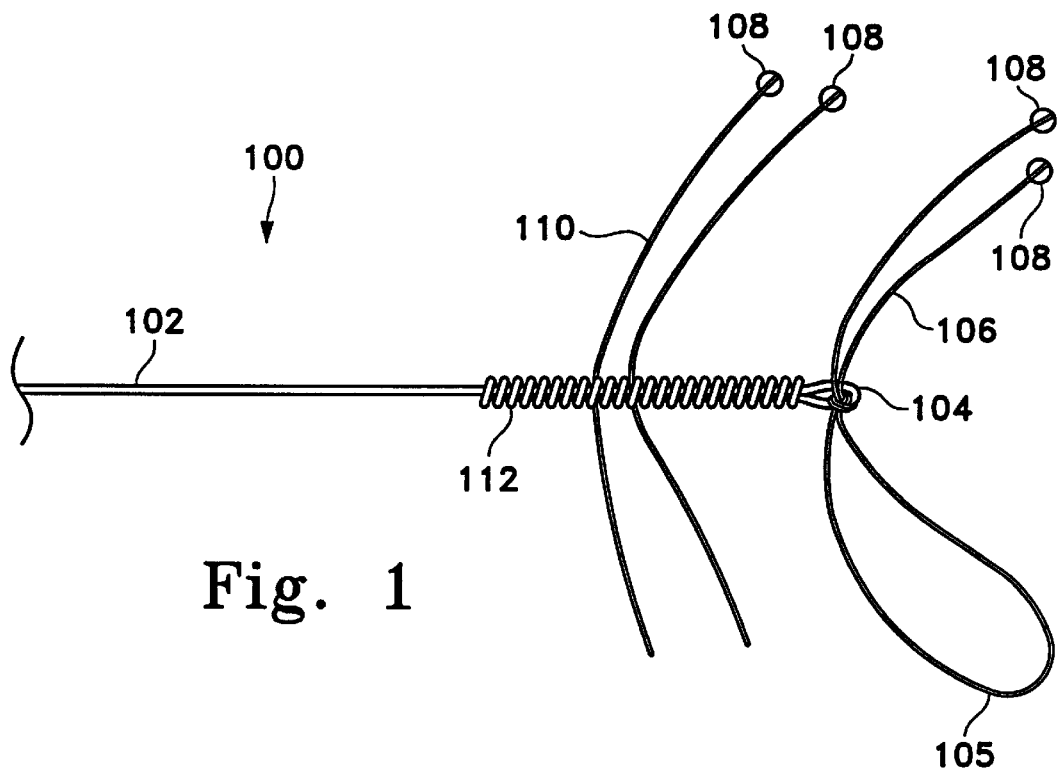
FIGS. 1 and 2 show side views of inventive retrievers made according to the invention.
Figure 2:
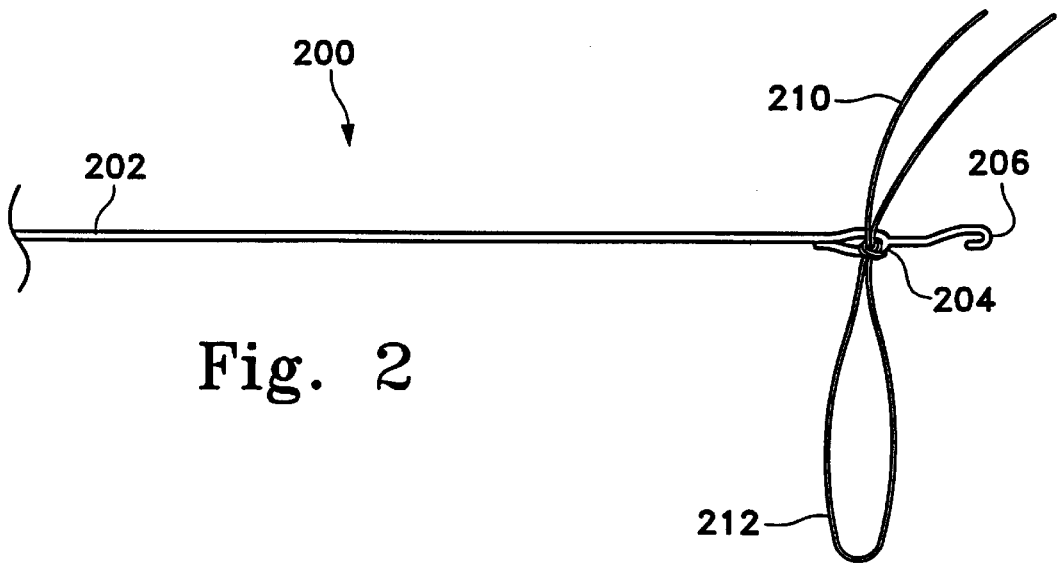

FIGS. 1 and 2 show two variations of the retrieval device made according to the invention. FIG. 1 shows a first variation (100). The principal components are a core wire (102), a loop (104) placed distally on core wire (102), one or more sets of fibers (106) extending through loop (104) and perhaps looping (as shown at (105)) or not, as desired. Small balls (108) may be placed at the loose ends of fiber (106). Other fibers (110) may be placed either through loop (104) or, as is shown in FIG. 1, a short proximal distance up core wire (102. These auxiliary fibers 1(10) may be tied on to the core wire 102) by filamentary wrapping (112) or by other acceptable attachment devices such as platinum wire coil.

In general, the core wire (102) may be of stainless steel acceptable for use in intravascular devices or may be of any other material which is known to be safe and efficacious in such practice. One common material is a series of nickel-titanium alloys, some of which are known as nitinol in the art. Suitable stainless steels include SS304, SS306, SS308, SS316, and SS318.

Preferred nickel-titanium alloys are usually super elastic. These materials are discussed at length in U.S. Pat. Nos. 3,174,851 to Buehler et al, 3,351,463 to Rozner et al, and 3,753,700 to Harrison et al. Commercial alloys containing as much as 8% or more of one or more members of the iron group, e.g., Fe, Cr, Co, are considered to be encompassed within the class of super-elastic nickel-titanium alloys suitable for this service. Most preferred are alloys containing 1.5 to 2.5% Cr and having a transition temperature of less than zero degrees Centigrade.

The core wire is constructed much in the way that typical endovascular guide wires are made. That is to say that the core wire is straightened, cleaned, and typically ground to a smaller point, e.g., a tapered distal end. The core wire needs to be flexible and torqueable so to allow it to be placed in a specific position within the human body. It may have an overall length of between 70 and 300 centimeters. The maximum outer diameter is often between 8 and 40 mils (thousands of an inch). The proximal portion of the wire (not shown in the Figures) is normally of a single diameter and having an overall length of 40 to about 250 centimeters. Often there is a section having an intermediate diameter between the proximal end and that of the distal end as shown in FIG. 1 and it might have a length of 15 to 60 centimeters. The most flexible section is the distal or end section (100) shown in FIG. 1. Its length is typically between 1 and 10 centimeters. Without limiting ourselves at all, the section of the retriever shown in FIG. 1 would rarely have a diameter any larger than 6 mils.

The loop (104) found at the distal end of this variation (100) of the invention, may be soldered or welded on to the distal end of the core wire (102). It is not necessary that the ring (104) be a discrete portion, it may be simply an end section of the core wire (102) folded upon itself and held in place by soldering or welding or other suitable joining procedure. The filaments (106) or (110) are usually no more than 2 to 4 centimeters in length. Said another way: the distance between the end of a particular filament (106) and its attachment point on the core wire (102) is rarely more than 2 to 4 centimeters from that core wire. The filaments may be made of any desirable material which is flexible and strong. Filaments (106) are fixedly attached to the loop (104) via, e.g., a knot, glue, tightness of loop (104), or by other suitable attachments. The materials making up the filaments (106) and (110) are, e.g., polyesters or polyamides, e.g., polyethylene terephthalate or Nylon. Both of these materials are flexible and strong and well recognized by the regulatory agencies around the world as being efficacious in medical devices. Of course, other polymeric materials would be suitable as well. It may be desirable to place small balls (108) or small helical coils at the cut ends of filaments (106) and (110). The placement of such balls is not necessary but when the inventive device is used to trap or gather or ensnare small diameter or soft vaso-occlusive helical coils, the balls provide an added measure of predictability in snaring and retaining the coils. Additionally, the coils or balls may be used as radio-opaque markers to assist in the snaring operation.

As depicted in FIG. 1, filament (106) has a loop (105) therein. The loop is not a requirement of the invention. It is, sometimes, a desirable variation. As with the platinum balls (108) listed above, the presence of a loop provides for some additional measure of predictability in ensnaring the desired vaso-occlusive devices or other devices in the vascular system.

Also shown in FIG. 1 are a pair, one or more, of filaments (110) placed more proximally up the core wire (102). The filaments (110) are shown to be singlets. They are depicted having balls (108) at one end and being bare at the other end. Various of these "flail" filaments (106) and (110) may be attached to the core wire (102) in a number of different ways. For instance, in FIG. 1 is shown the use of filamentary wrap (112). This is a wrap using a polymeric filament put on much in a way an eyelet on a fishing pole is included. It is also within the scope of this invention that radio-opaque materials such as platinum, platinum alloys or gold wires be used to attach filaments (106) or (108) to core wire (102). The radio-opaque coils (112) are wrapped in somewhat standard fashion as is typically done in assembling a guidewire. Such portion of the inventive device is desirable and it provides the physician using the device with an indication via fluoroscope of the position of the usually radiolucent fibers (106) and (110) relative to the object to be removed from the body. When radio-opaque materials are used for the beads or balls (108) placed at the tip of the filaments (106) or (110), the radio-opacity also helps locate the active portion of the retrieval device with respect to the object to be removed from the body.

FIG. 2 shows another variation of the inventive device (200). In this variation, core wire (202) also includes a loop (204) and a small guarded hook (206). The filaments (210) pass through loop (204) and are generally of the same construction with or without loop (212) as the filaments discussed with regard to FIG. 1 above. These filaments (210) are shown to be used without any terminator on their various tips. This, again, is a matter of choice for the designer of a particular retrieval device made according to this invention. It is also within the scope of this invention to exclude the loop (104) in FIG. 1 or loop (204) in FIG. 2 and use only some other means for attaching the fibers to the core wire (102) or (202) respectively.

The hook (206) shown at FIG. 2 is optional. It may be used to entwine an artifact left or found within an opening in the human body. Preferably, the hook (206) is of the general shape shown in FIG. 2. That is to say that the end of the hook is in a general line with the axis of core wire (202). This configuration places the hook in such a position that it does not normally grab or snare biological material as might be found on the walls of the opening or lumen into which this retriever assembly is placed. Other hook shapes are of course acceptable for this invention.

Figure 3:
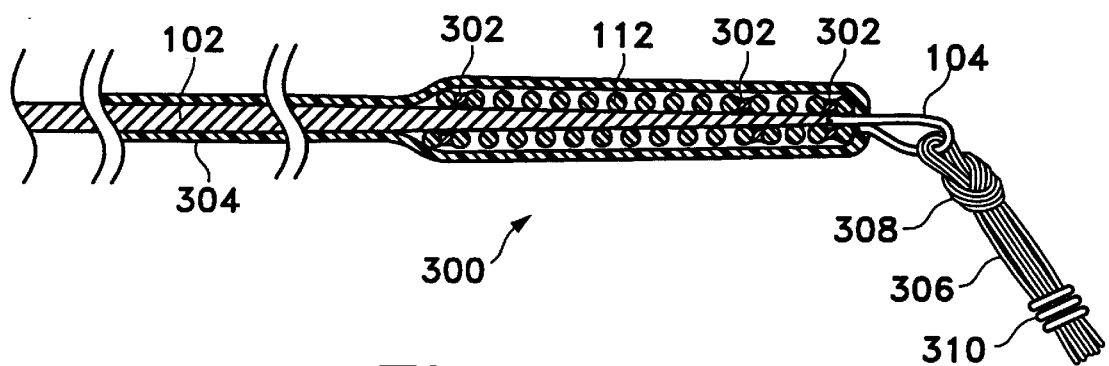
FIGS. 3 and 4 show partial cutaway side views of inventive retrievers made according to the invention.

FIG. 3 shows a highly desirable variation of the invention in which the retriever (300) includes a distal coil (112) as shown in FIG. 1 which does not capture any filamentary material. The coil (112) is soldered to the core wire (102) at a number of sites (302) to secure it in place. The coil (112) may optionally be covered with a polymeric sheath (304). The polymeric sheath (304) would typically extend from the distal tip of the core wire (102) incorporating the distal loop (104) to some location proximal of the proximal-most portion of the coil (112). The polymeric sheath (304) may have a variety of advantages; it serves to prevent the entwining fibers (306) from becoming entwined in the coil (112) and, if the proper polymer is chosen as a constituent of the polymeric sheath (304), the sheath (304) is lubricious and aids in the passage of the retriever assembly (300) through the catheter used to place the retriever at the selected body site.

The variation (300) found in FIG. 3 utilizes a group of fibers as the fiber bundle (306) using a knot (308) to maintain the bundle (306) in place. The bundle (306) uses a small radio-opaque coil (310) of perhaps 3 to 5 turns at the end of the bundle (306). The tip of bundle (306) may be secured using the step of melting the polymers to form a terminator.

A desirable retriever built using the variation shown in FIG. 3 and having an overall diameter of 13 to 20 mils, may have a core wire (102) of either stainless steel or superelastic alloys (preferably titanium-nickel) covered with a polyfluorocarbon polymeric sheath (304) having a wall thickness of 1.5 to 3.0 mils. The polymeric sheath might be of a length between 30 and 50 centimeters and of a suitably lubricious material, e.g., Teflon or polyurethane or the like. The coil (112) would typically have a length between 8 and 20 centimeters. The core wire (102) tapers from an overall diameter of 13 to 20 mils to about 2 to 5 mils in the vicinity of the loop (104). The fiber bundle (306) is often in the neighborhood of 3 to 5 centimeters from end-to-end. The fiber bundle (306) should be able to fold over the distal end of the core wire (102) without binding in the lumen of the delivery catheter. These dimensions are for the purpose of illustrating the overall size of the device and are not for the purpose of limiting the scope of the invention in any way.

Figure 4:
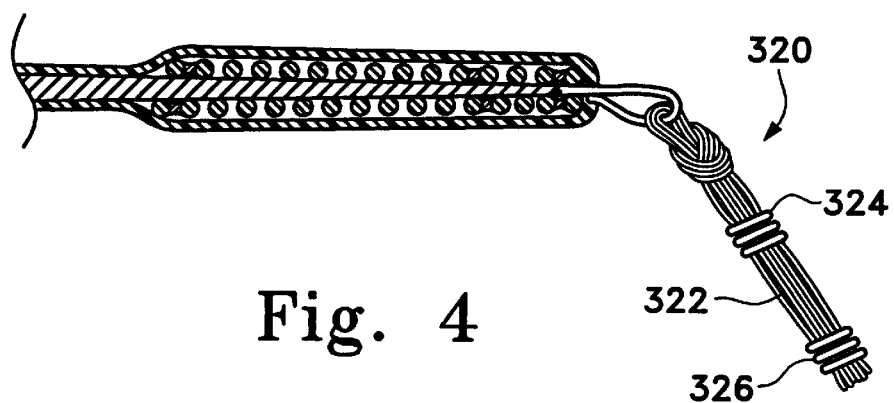

FIG. 4 shows a further variation (320) in which the fiber bundle (322) has both a proximal coil (324) and a distal coil (326).

Figure 5A:
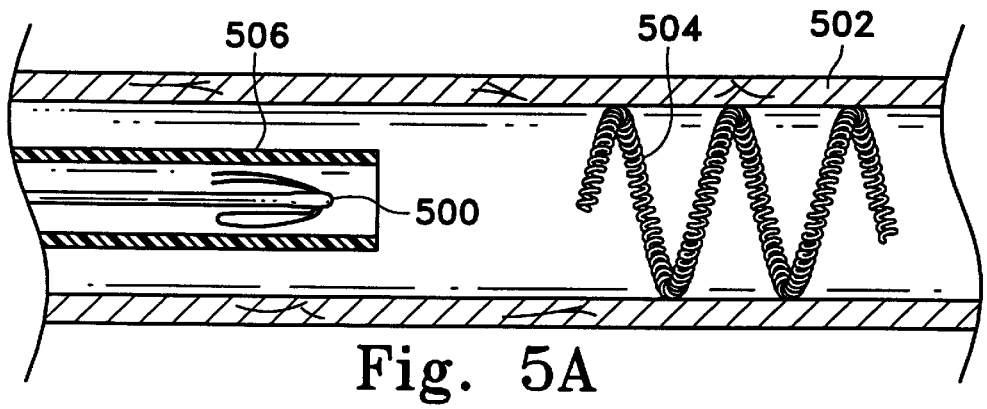
FIGS. 5A–5D show a procedure for using the inventive retriever in removing an undesired vaso-occlusive device from within an opening in the human body.
Figure 5B:
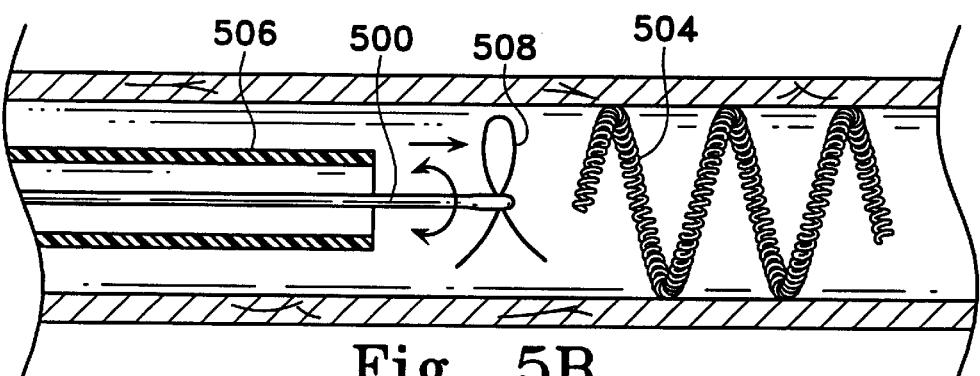

FIGS. 5A to 5D show a method of using this retrieval device to retrieve a body from within a vessel. As is seen in FIG. 5A, the device (500) is inserted into a vessel (502) so that the distal end of the device (500) is adjacent to the body to be removed from the vessel. In the depicted instance, the body to be removed is a helically wound vaso-occlusive coil (504). The insertion of the retriever assembly (500) to such a location is accomplished by conventional technology. That is to say that a catheter (506) may be used in conjunction with a separate guide wire (not shown) and the catheter/guidewire assembly inserted to the selected site using a known technique. Once the retriever assembly (500) is adjacent to the vaso-occlusive coil (504) to be removed, the retriever assembly (500) is pushed from the distal end of catheter (506). The retriever device (500) is both twisted and pushed so that the filaments (508) found on the distal tip of the retriever device (500) are advanced, with turning, to vaso-occlusive coil (504). The step of advancing and twisting is shown in FIG. 5B.

Figure 5C:
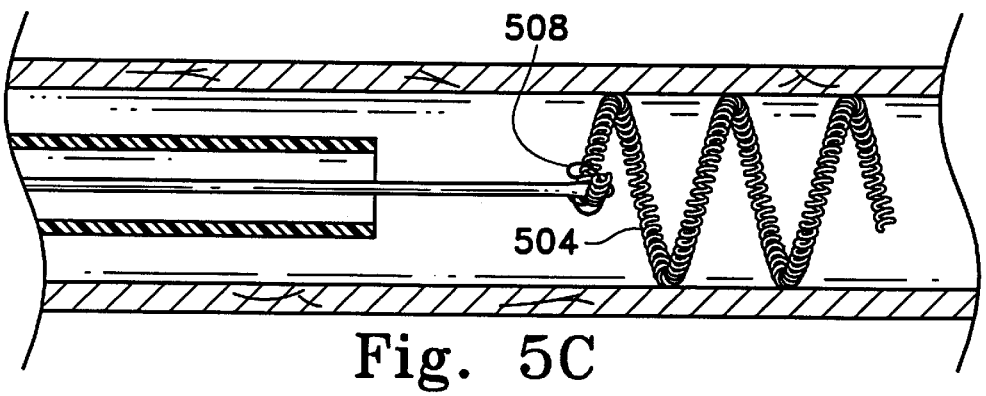
Figure 5D:
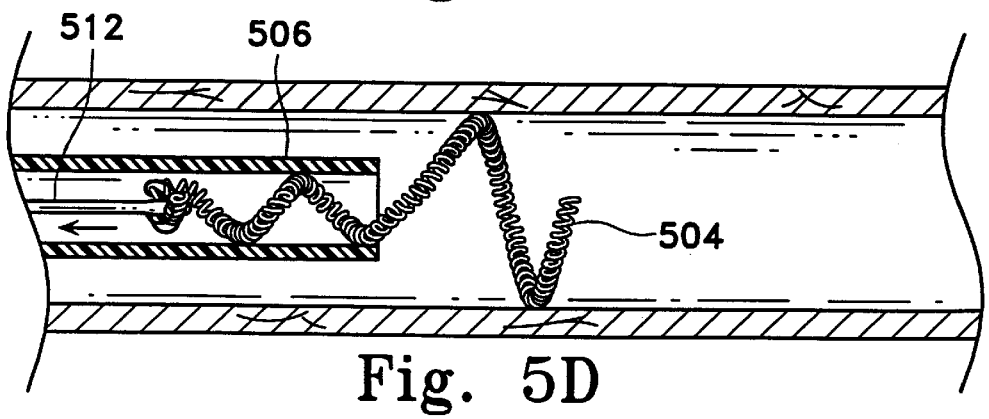

FIG. 5C shows the filaments (508) intertwined with the proximal end of vaso-occlusive coil (504). It should be noted that the inventive device (500) is especially useful for retrieving small helical coils from the vascular system of the body. This is so because the multiplicity of fibers found on the distal end of the retriever device (500) is quite likely to enter the gaps between the various turns of the helical coil (304) shown in the Figures. These inventive devices are useful for other artifacts found in openings in the lumens within the human body, but the fibers are especially useful for retrieval of small helically-wound coils.

Once the artifact (504) is engaged by fibers (508) as shown in FIG. 5C, the core wire may be retracted through the lumen of catheter (506) by tugging coil (504) along into the catheter end. Once the artifact is safely trapped by the catheter or within the catheter, the catheter assembly with its enclosed or trailing vaso-occlusive device may be withdrawn into larger catheters and thence to without the body.

This invention has been described and specific examples of the invention have portrayed. The use of those specifics is not intended to limit the invention in any way. Additionally, to the extent that there are variations of the invention which are within the spirit of the disclosure and yet are equivalent to the inventions found in the claims, it is our intent that those claims cover the variations as well.

We claim as our invention:

1. A medical retrieval device comprising:
   a.) an elongate core wire having a proximal and a distal end formed into a loop, and
   b.) at least one flexible polymeric fiber comprising a multiplicity of fibers fixedly and distally attached to said elongate core wire passing through said loop and knotted thereto and firther having a region remote from said core wire, and
   c.) at least one radiopaque marker fixedly attached to said flexible fiber.

2. The medical retrieval device of claim 1 wherein said at least one radio-opaque marker comprises a ball.

3. The medical retrieval device of claim 1 wherein said at least one radio-opaque marker comprises coil.

4. The medical retrieval device of claim 1 further comprising a hook located distally on said core wire.

5. The medical retrieval device of claim 1 wherein said at least one flexible fiber comprises at least one loop.

6. The medical retrieval device of claim 1 wherein the radio-opaque marker is fixedly attached to said fiber remote region.

7. The medical retrieval device of claim 6 wherein said radio-opaque marker comprises a ball.

8. The medical retrieval device of claim 6 wherein said radio-opaque marker comprises a coil.

9. The medical retrieval device of claim 1 further comprising a multiplicity of flexible fibers located proximally of said at least one flexible fiber and fixedly attached to said core wire.

10. The medical retrieval device of claim 9 wherein said multiplicity of flexible fibers located proximally of said at least one flexible fiber are fixedly attached to said core wire with a fiber or wire wrapping.

11. The medical retrieval device of claim 10 wherein said fiber or wire wrapping comprises a material selected from the group consisting of polymers, metals, and alloys.

12. The medical retrieval device of claim 10 wherein said fiber or wire wrapping comprises a platinum alloy coil.

13. The medical retrieval device of claim 10 wherein said fiber or wire wrapping comprises a polymeric fiber.

14. The medical retrieval device of claim 10 wherein said core wire comprises a stainless steel.

15. The medical retrieval device of claim 10 wherein said core wire comprises a super-elastic alloy.

16. The medical retrieval device of claim 10 wherein said core wire comprises a super-elastic nickel-titanium alloy.

17. The medical retrieval device of claim 1 further comprising a coil wrapped coaxially and distally about said core wire.

18. The medical retrieval device of claim 17 further comprising a polymeric sheath coaxially about at least a portion of said coil.

19. The medical retrieval device of claim 18 wherein said polymeric sheath comprises a lubricious polymer.

20. The medical retrieval device of claim 19 wherein said polymeric sheath comprises polytetrafluoroethylene.

21. A medical retrieval device comprising:
 a.) an elongate core wire having proximal and distal ends and wherein said elongate core distal end is folded back to form a distal loop on said elongate core wire, and
 b.) a multiplicity of fibers comprising at least one loop fixedly attached to said distal loop of said elongate core wire and said multiplicity of fibers has a region remote from said core wire and further includes a radiopaque marker fixedly attached to said fiber remote region.

22. The medical retrieval device of claim 21 wherein said radiopaque marker comprises a ball.

23. The medical retrieval device of claim 21 wherein said radiopaque marker comprises a coil.

24. The medical retrieval device of claim 21 further comprising a multiplicity of flexible fibers located proximally of said at least one flexible fiber and fixedly attached to said core wire.

25. The medical retrieval device of claim 24 wherein said multiplicity of flexible fibers located proximally of said at least one flexible fiber are fixedly attached to said core wire with a fiber or wire wrapping.

26. The medical retrieval device of claim 25 wherein said fiber or wire wrapping comprises a material selected from the group consisting of polymers, metals, and alloys.

27. The medical retrieval device of claim 25 wherein said fiber or wire wrapping comprises a platinum alloy coil.

28. The medical retrieval device of claim 25, wherein said fiber or wire wrapping comprises a polymeric fiber.

29. The medical retrieval device of claim 25, wherein said core wire comprises a stainless steel.

30. The medical retrieval device of claim 25 wherein said core wire comprises a super-elastic alloy.

31. The medical retrieval device of claim 25 wherein said core wire comprises a super-elastic nickel-titanium alloy.

32. The medical retrieval device of claim 21 further comprising a coil wrapped coaxially distally about said core wire.

33. The medical retrieval device of claim 32 further comprising a polymeric sheath coaxial with at least a portion of said coil.

34. The medical retrieval device of claim 33 wherein said polymeric sheath comprises a lubricious polymer.

35. The medical retrieval device of claim 34 wherein said polymeric sheath comprises polytetrafluoroethylene.

* * * * *